United States Patent [19]

Kulcsár et al.

[11] Patent Number: 4,904,647

[45] Date of Patent: Feb. 27, 1990

[54] ANTIMICROBIAL PHARMACEUTICAL COMPOSITION

[75] Inventors: Gábor Kulcsár; Judit Frank; Péter Sárközy; Katalin Kálóy, all of Budapest, Hungary

[73] Assignee: Chinoin Gyogyszer-es Vegyeszeti Termekek Gyara Rt, Budapest, Hungary

[21] Appl. No.: 222,056

[22] Filed: Jul. 20, 1988

[30] Foreign Application Priority Data

Jul. 20, 1987 [HU] Hungary ............................. 3335/87

[51] Int. Cl.$^4$ ............................................ A61K 31/65
[52] U.S. Cl. ..................................... 514/154; 514/152
[58] Field of Search ............... 514/152, 154, 291, 300, 514/312

[56] References Cited

U.S. PATENT DOCUMENTS

| | | | |
|---|---|---|---|
| 3,497,594 | 2/1970 | Johnston | 514/154 |
| 4,147,788 | 4/1979 | Lee | 514/291 |
| 4,517,191 | 5/1985 | Wentland et al. | 514/300 |

*Primary Examiner*—Leonard Schenkman
*Attorney, Agent, or Firm*—Herbert Dubno; Jonathan Myers

[57] ABSTRACT

The invention relates to a synergistic, antimicrobial pharmaceutical composition containing 0.01 to 50% by weight of a quinolinecarboxylic acid derivative or a naphthyridinecarboxylic acid derivative of the formula (I),

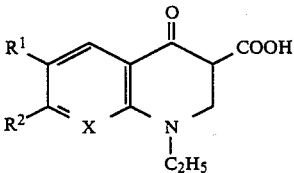

wherein
X is carbon or nitrogen;
$R^1$ is hydrogen or fluorine;
$R^2$ is methyl, piperazino or methylpiperazino group; or
$R^1$ and $R^2$ together are a methylenedioxy group; and
0.01 to 95% by weight of a tetracycline derivative of the formula (II),

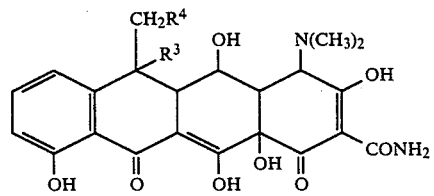

wherein
$R^3$ and $R^4$ are hydrogen; or
$R^3$ and $R^4$ together represent an additional chemical bond, in 20:1 to 1:50 ratio of the compound of the formula (I) to the compound of the formula (II), optionally in an admixture with an amount required to 100% by weight of an inert, solid or liquid carrier such as magnesium carbonate, magnesium stearate, starch, talc, cyclodextrine or water and other additives such as filling, disintegrating, sliding and emulsifying agents.

6 Claims, No Drawings

ANTIMICROBIAL PHARMACEUTICAL COMPOSITION

FIELD OF THE INVENTION

This invention relates to synergistic, antimicrobial pharmaceutical compositions containing a quinolinecarboxylic acid derivative or a naphthyridinecarboxylic acid derivative of the formula (I),

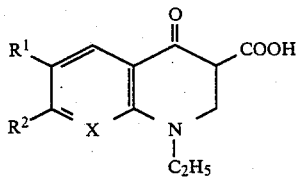

wherein
X is carbon or nitrogen;
$R^1$ is hydrogen or fluorine;
$R^2$ is methyl, piperazino or methylpiperazino group; or
$R^1$ and $R^2$ together are a methylenedioxy group; and a tetracycline derivative of the formula (II),

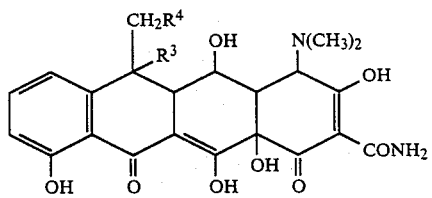

wherein
$R^3$ and $R^4$ are hydrogen; or
$R^3$ and $R^4$ together represent an additional chemical bond,
as active ingredients.

In an other aspect of the invention, there is provided a process for the preparation of these compositions.

BACKGROUND OF THE INVENTION

In antimicrobial therapy, a continuous battle exists between the adaptation capability of microorganisms (development of resistance) and the preparation of novel drugs.

In the case of novel drugs, the adaptation capability, i.e. the resistance usually develops within a shorter or longer period. It can be expected that the development of the resistance becomes particularly rapid when the new substance is a derivative of a drug previously used for a long time since in this case, the resistance developed to the starting compound will of course more rapidly be modified for the derivatives.

The development of the resistance can be delayed by the simultaneous administration, i.e. combination of several active compounds whereby the metabolism of the microorganisms is attacked at several points at the same time. This results that the resistance of the microorganisms to the combination hardly or long afterwards develops thus, the desired "microbicidal" (killing) effect is strengthened.

In antimicrobial therapy, nalidixic acid has been used for a long time as active ingredient. It was published that from its derivatives, norfloxacin (Belgian patent specification No. 863,429) and pefloxacin (Belgian patent specifications Nos. 870,576 and 870,917) show a highly favorable effect on gram-negative pathogens whereas their effect on gram-positive pathogens is more moderate.

Tetracycline is also a long-known antimicrobial substance. Out of its derivatives, doxycycline has a very favorable effect on gram-positive pathogens and a moderate effect on gram-negative ones.

OBJECT OF THE INVENTION

The aim of the invention is to prepare broad-spectrum pharmaceutical compositions by combining these two types of active substances and thereby to inhibit the development of resistance.

DESCRIPTION OF THE INVENTION

In combining tetracycline derivatives with the quinioline-carboxylic acid derivatives or naphthyridinecarboxylic acid derivatives of the formula (I), it has been surprisingly observed that, in addition to the realization of the aim of the invention, a high-level synergistic action of these two types of active substances occurred, whereby the effective doses could strongly be decreased with the important advantages of less side-effects and a cheaper therapy.

Thus, the present invention relates to the preparation of a synergistic, antimicrobial pharmaceutical composition containing a quinolinecarboxylic acid derivative or a naphthyridinecarboxylic acid derivative of the formula (I), wherein
X is carbon or nitrogen;
$R^1$ is hydrogen or fluorine;
$R^2$ is methyl, piperazino or methylpiperazino group; or
$R^1$ and $R^2$ together are a methylenedioxy group; and a tetracycline derivative of the formula (II), wherein
$R^3$ and $R^4$ are hydrogen; or
$R^3$ and $R^4$ together represent an additional chemical bond,
as active ingredients, which comprises mixing together 0.01 to 50% by weight of a quinolinecarboxylic acid derivative or a naphthyridinecarboxylic acid derivative of the formula (I), wherein X, $R^1$ and $R^2$ are the same as defined above and 0.01 to 95% by weight of a tetracycline derivative of the formula (II), wherein $R^3$ and $R^4$ are the same as defined above while maintaining the ratio of the compound of the formula (I) to the compound of the general formula (II) as 1:1 to 1:20, and optionally inert, solid or liquid carriers, preferably magnesium carbonate, magnesium stearate, starch, talc, cyclodextrin or water as well as binding, disintegrating, emulsifying, sliding agents and lubricants as additives and formulating them in a known way to a pharmaceutical composition suitable for therapeutical application.

In the process of the invention, preferably a compound of the formula (I), wherein X, $R^1$ and $R^2$ are as defined above, suitably norfloxacin (1,4-dihydro-1-ethyl-6-fluoro-4-oxo-7-piperazinoquinoline-3-carboxylic acid) and doxycycline (4-dimethylamino-1,11-dioxo-6-methyl-1,4,4a,5,5a,6,11,12a-octahydro-3,5,10,12,12a-pentahydroxy-2-naphthacenecarboxamide) may be used as active ingredients of the combination.

Similarly, oxolinic acid (1,4-dihydro-1-ethyl-6,7-methylenedioxy-4-oxoquinoline-3-carboxylic acid) and methacycline (4-dimethylamino-1,11-dioxo-6-methylene-1,4,4a,5,5a,6,11,12a-octahydro-3,5,10,12,12a-pentahydroxy-2-naphthacenecarboxamide) may preferably be used in the combination according to the invention.

According to a preferred embodiment of the invention, the active ingredients are used in 1:1 ratio. If desired, the compositions may contain also other active ingredients, (such as antibiotics, chemotherapeutics or the like).

The pharmaceutical compositions according to the invention may be formulated in solid forms, such as granulates, tablets, capsules, dragées and suppositories, semisolid forms, such as ointments and the like or liquid forms, such as injectable solutions, emulsions or suspensions. Preferably gels, ointments, dusting powders for wounds, injectable solutions and suspensions as well as the combinations of powder and solvent ampoules are prepared.

Depending on the formulation, magnesium carbonate, magnesium stearate, starch, talc and water as commonly used carriers, cyclodextrin as a novel carrier as well as other additives such as vehicles, disintegrating, sliding and emulsifying agents may be used.

The compositions according to the invention may be administered by oral, parenteral or rectal route or may be topically used.

The orally useful compositions are e.g. granulates, tablets, capsules or dragées. Parenterally useful compositions are e.g. the aqueous emulsions, suspensions or solutions. Ointments, aqueous or oily emulsions and suspensions as well as sprays may topically be applied.

The pharmaceutical compositions containing the synergistic active ingredient combination may be used in the veterinary medicine, too, e.g. in the form of a powder mixed with the fodder, or in the form of a solution added to the drinking fluid of the animals. For this purpose, compositions containing a combination of oxolinic acid and methacrycline are preferably used.

The in vitro biological activity of the compositions according to the invention are shown in Tables I to V.

The international resistant and/or polyresistant human-pathogenic and/or veterinary-pathogenic microorganisms used in these investigations were as follows.
(1) *Vibrio parahaemolyticus:* CCM.5938.
(2) *Pseudomonas fluorescens:* CCM.2115.
(3) *Pseudomonas pictorum:* CCM.284.
(4) *Pseudomonas acidovorans:* CM.283.
(5) *Proteus vulgaris:* CCM.1799.
(6) *Proteus mirabilis:* CCM.1944.
(7) *Shigella sonnei:* CCM.1373.
(8) *Salmonella typhimurium:* CCM.5445.
(9) *Salmonella cholerae suis:* CCM.5438.
(10) *Escherichia coli:* DSM.30038.
(11) *Escherichia coli:* CCM.5863.
(12) *Escherichia coli:* CCM.5172.
(13) *Klebsiella pneumoniae:* CCM.1848.
(14) *Serratia marcescens:* CCM.303.
(15) *Pasteurella multocida:* CCM.5419.
(16) *Staphlococcus aureus:* CCM.885.
(17) *Staphylococcus aureus:* CCM.2317.
(18) *Staphylococcus aureus:* CCM.2326.
(19) *Streptococcus agalactiae:* CCM.5534.
(20) *Streptococcus disgalactiae:* CCM.5548.
(21) *Bacillus subtilis:* ATCC.6633.
(22) *Micrococcus flavus:* ATCC.10240.
(23) *Bacillus licheniformis:* CCM.2182.
(24) *Bacillus licheniformis:* CCM.2205.
(25) *Pseudomonas putrefaciens:* Sz-III-156.
(26) *Pseudomonas fluorescens putida:* M-III-21.
(27) *Pseudomonas fluorescens putida:* K-I-86.

Abbreviations usedhereinabove and hereinafter are as follows:
ATCC=The American Type Culture Collection
CCM=Czechoslovak Collection of Microorganisms
DSM=Deutsche Sammlung für Mikroorganismen
µg/ml=microgram/milliliter The investigations were carried out on a Difco Bouillon medium (in the case of bacteria) or on a modified Difco Bouillon medium (in the case of vibrios).

The inoculation was made with a germ number of $5 \times 10^5$/ml. The incubation lasted 24 hours at 37° C.

It is obvious from the data of the Tables that, due to the synergistic effect, from the combination a part and in some cases even a fraction of the amounts of the active ingredients, (as calculated for their individual activity), is sufficient to achieve an identical effect.

TABLE I

Combination of Nalidixic Acid with Doxycycline

| | | MIC value µg/ml | | | | Percentage of the MIC value in the combination % | | | Effect, % | |
|---|---|---|---|---|---|---|---|---|---|---|
| | | 1 | 2 | 3 Combination Nal | 4 Combination Dox | 5 Nal | 6 Dox | 7 Nal + Dox | 8 Additive | 9 Synerg. |
| Column Number | | Nal | Dox | | | | | | | |
| *Vibrio p. haemolyticus* | CCM. 5938. | 5 | 0.5 | 0.5 | 0.25 | 10 | 50 | 30 | 60 | 40 |
| *Pseudomonas pictorum* | CCM. 284. | 25 | 0.75 | 2.5 | 0.075 | 10 | 10 | 10 | 20 | 80 |
| *Proteus vulgaris* | CCM. 1799. | 50 | 10 | 5 | 2.5 | 10 | 25 | 16.5 | 35 | 65 |
| *Proteus mirabilis* | CCM. 1944. | 10 | 25 | 2.5 | 5 | 25 | 20 | 22.5 | 45 | 55 |
| *Salmonella typhimurium* | CCM. 5445. | 50 | 10 | 5 | 5 | 10 | 50 | 30 | 60 | 40 |
| *Salmonella cholerae suis* | CCM. 5438. | 25 | 0.5 | 2.5 | 0.05 | 10 | 10 | 10 | 20 | 80 |
| *Escherichia coli* | DSM. 30038. | 50 | 5 | 5 | 0.5 | 10 | 10 | 10 | 20 | 80 |
| *Escherichia coli* | CCM. 5863. | 25 | 5 | 2.5 | 0.5 | 10 | 10 | 10 | 20 | 80 |
| *Escherichia coli* | CCM. 5172. | 50 | 2.5 | 5 | 0.5 | 10 | 20 | 15 | 30 | 70 |
| *Pasteurella multocida* | CCM. 5419. | 50 | 0.25 | 5 | 0.025 | 10 | 10 | 10 | 20 | 80 |
| *Staphylococcus aureus* | CCM. 2317. | 100 | 0.25 | 10 | 0.05 | 10 | 20 | 25 | 30 | 70 |
| *Staphylococcus aureus* | CCM. 2326. | 100 | 0.25 | 10 | 0.075 | 10 | 30 | 20 | 40 | 60 |
| *Streptococcus disgalactiae* | CCM. 5548. | 75 | 0.5 | 10 | 0.25 | 13.3 | 50 | 31.6 | 63.3 | 36.7 |

Abbreviations:
Nal = nalidixic acid
Dox = doxycycline

TABLE II

Combination of Oxolinic acid with Doxycycline

| Column Number | | MIC value μg/ml | | Combination | | Percentage of the MIC value in the combination % | | | Effect, % | |
|---|---|---|---|---|---|---|---|---|---|---|
| | | 1 | 2 | 3 | 4 | 5 | 6 | 7 | 8 | 9 |
| | | Ox | Dox | Ox | Dox | Ox | Dox | Ox + Dox | Additive | Synerg. |
| Vibrio p-Haemolyticus | CCM. 5938. | 1 | 0.5 | 0.1 | 0.25 | 10 | 50 | 30 | 60 | 40 |
| Pseudomonas fluorescens | CCM. 2115. | 10 | 0.5 | 0.25 | 0.25 | 2.5 | 50 | 26.3 | 52.5 | 47.5 |
| Pseudomonas acidovorans | CCM. 283. | 0.5 | 0.25 | 0.05 | 0.05 | 10 | 20 | 15 | 30 | 70 |
| Pseudomonas pictorum | CCM. 284. | 5 | 0.75 | 0.5 | 0.075 | 10 | 10 | 10 | 20 | 80 |
| Shigella sonnei | CCM. 1373. | 0.75 | 1 | 0.075 | 0.05 | 10 | 5 | 7.5 | 15 | 85 |
| Escherchia coli | CCM. 5863. | 5 | 5 | 0.75 | 0.75 | 15 | 15 | 15 | 30 | 70 |
| Escherichia coli | CCM. 5172. | 2.5 | 2.5 | 0.75 | 0.75 | 30 | 30 | 30 | 60 | 40 |
| Staphylococcus aureus | CCM. 885. | 25 | 1 | 2.5 | 0.1 | 10 | 10 | 10 | 20 | 80 |
| Staphylococcus Aureus | CCM. 2317. | 10 | 0.25 | 1 | 0.025 | 10 | 10 | 10 | 20 | 80 |
| Bacillus subtilis | ATCC. 6633. | 0.75 | 0.05 | 0.1 | 0.025 | 13.3 | 50 | 31.6 | 63.3 | 36.7 |
| Bacillus cereus | CCM. 2010. | 5 | 0.5 | 0.5 | 0.25 | 10 | 50 | 30 | 60 | 40 |

Abbreviations:
Ox = oxolinic acid
Dox = doxycycline

TABLE III

Combination of Norfloxacin with Doxycycline

| Column Number | | MIC value μg/ml | | Combination | | Percentage of the MIC value in the combination % | | | Effect, % | |
|---|---|---|---|---|---|---|---|---|---|---|
| | | 1 | 2 | 3 | 4 | 5 | 6 | 7 | 8 | 9 |
| | | Norf | Dox | Norf | Dox | Norf | Dox | Norf + Dox | Additive | Synerg. |
| Vibrio p. haemolyticus | CCM. 5938 | 0.5 | 0.5 | 0.25 | 0.1 | 50 | 20 | 35 | 70 | 30 |
| Pseudomonas fluorescens | CCM. 2115. | 0.25 | 0.5 | 0.05 | 0.05 | 20 | 10 | 15 | 30 | 70 |
| Pseudomonas pictor. | CCM. 284. | 0.75 | 0.75 | 0.1 | 0.25 | 13.3 | 33.3 | 23.3 | 46.6 | 53.4 |
| Proteus vulg. | CCM. 1799. | 0.1 | 10 | 0.01 | 5 | 10 | 50 | 30 | 60 | 40 |
| Shigella sonnei | CCM. 1373. | 0.1 | 1 | 0.01 | 0.5 | 10 | 50 | 30 | 60 | 40 |
| Salmon. typhimus. | CCM. 5445. | 0.5 | 10 | 0.075 | 2.5 | 15 | 25 | 20 | 40 | 60 |
| Salmon. Choleraesuis | CCM. 5438. | 0.5 | 0.5 | 0.05 | 0.05 | 10 | 10 | 10 | 20 | 80 |
| Esch. Coli | DSM. 30038. | 0.1 | 5 | 0.025 | 0.75 | 25 | 15 | 20 | 40 | 60 |
| Esch. coli | CCM. 5863. | 0.25 | 5 | 0.05 | 0.75 | 20 | 15 | 17.5 | 35 | 65 |
| Past. multocida | CCM. 5419. | 0.5 | 0.25 | 0.05 | 0.025 | 10 | 10 | 10 | 20 | 80 |
| Staph. aureus | CCM. 885. | 5 | 1 | 1 | 0.25 | 20 | 25 | 22.5 | 45 | 55 |
| Strept. disgalact. | CCM. 5548. | 2.5 | 0.5 | 0.75 | 0.1 | 30 | 20 | 25 | 50 | 50 |

Abbreviations:
Norf + Norfloxacin
Dox = doxycycline

TABLE IV

Combination of Pefloxacin with Doxycycline

| Column Number | | MIC value μg/ml | | Combination | | Percentage of the MIC Value in the combination % | | | Effect, % | |
|---|---|---|---|---|---|---|---|---|---|---|
| | | 1 | 2 | 3 | 4 | 5 | 6 | 7 | 8 | 9 |
| | | Pefl | Dox | Pefl | Dox | Pefl | Dox | Pefl + Dox | Additive | Synerg. |
| Vibrio p. haemolyticus | CCM. 5938. | 0.5 | 0.5 | 0.75 | 0.25 | 15 | 50 | 32.5 | 65 | 35 |
| Proteus vulgaris | CCM. 1799. | 0.5 | 10 | 0.1 | 0.05 | 20 | 0.5 | 10.2 | 20.5 | 79.5 |
| Proteus mirabilib | CCM. 1944. | 0.5 | 25 | 0.075 | 2.5 | 15 | 10 | 12.5 | 25 | 75 |
| Shigella sonnei | CCM. 1373. | 0.25 | 1 | 0.05 | 0.1 | 20 | 10 | 15 | 30 | 70 |
| Salmon. typhimur | CCM. 5445. | 2.5 | 10 | 0.5 | 2.5 | 20 | 25 | 22.5 | 45 | 55 |
| Salmon. choleraesuis | CCM. 5438. | 1 | 0.5 | 0.1 | 0.05 | 10 | 10 | 10 | 20 | 80 |
| Esch. coli | DSM. 30038. | 1 | 5 | 0.1 | 0.5 | 10 | 10 | 10 | 20 | 80 |
| Esch. coli | CCM. 5863. | 1 | 5 | 0.1 | 1 | 10 | 20 | 15 | 30 | 70 |
| Klebs. pneumon. | CCM. 1848. | 0.75 | 2.5 | 0.075 | 1 | 10 | 40 | 25 | 50 | 50 |
| Serratia marcesc. | CCM. 303. | 0.5 | 25 | 0.1 | 10 | 20 | 40 | 30 | 60 | 40 |
| Past. multocida | CCM. 5419. | 0.25 | 0.25 | 0.05 | 0.05 | 20 | 20 | 20 | 40 | 60 |
| Strept. disgalact. | CCM. 5548. | 10 | 0.5 | 1 | 0.25 | 10 | 50 | 30 | 60 | 40 |
| Pseud. putrefac. | Sz-III-156. | 0.25 | 0.5 | 0.05 | 0.075 | 20 | 15 | 17.5 | 35 | 65 |
| Pseud. fluoresc. putida | M-III-21. | 2.5 | 2.5 | 0.5 | 0.75 | 20 | 30 | 25 | 50 | 50 |
| Pseud. flouresc. putida | K-I-86. | 2.5 | 0.25 | 0.05 | 0.05 | 2 | 20 | 11 | 22 | 78 |

Abbreviations:
Pefl = pefloxacin
Dox = doxycycline

TABLE V

| | | \multicolumn{4}{c|}{Combination of Oxolinic acid with Methacycline} | | | | | |
|---|---|---|---|---|---|---|---|---|---|---|
| | | \multicolumn{4}{c|}{MIC value μg/ml} | \multicolumn{3}{c|}{Percentage of the MIC value in the combination %} | \multicolumn{2}{c|}{Effect, %} |
| | | 1 | 2 | \multicolumn{2}{c|}{3 Combination} | 5 | 6 | 7 | 8 | 9 |
| Column Number | | Ox | Methac | Ox | Methac | Ox | Methac | Ox + Methac | Additive | Synerg. |
| *Vibrio p. haemolyticus* | CCM. 5938. | 1 | 1 | 0.25 | 0.1 | 25 | 10 | 17.5 | 35 | 65 |
| *Pseud. fluoresc.* | CCM. 2115. | 2.5 | 0.5 | 0.75 | 0.1 | 30 | 20 | 25 | 50 | 50 |
| *Esch. coli* | DSM. 30038. | 1 | 2.5 | 0.25 | 0.25 | 25 | 10 | 17.5 | 35 | 65 |
| *Esch. coli* | CCM. 5863. | 5 | 2.5 | 0.25 | 0.25 | 5 | 10 | 7.5 | 15 | 85 |
| *Esch. coli* | CCM. 5172. | 2.5 | 2.5 | 0.25 | 0.25 | 10 | 10 | 10 | 20 | 80 |

Abbreviations:
Ox = oxolinic acid
Methac = methacycline

We claim:

1. A synergistic, antimicrobial pharmaceutical composition which comprises 0.01 to 50% by weight of a quinolinecarboxylic acid derivative or a naphthyridinecarboxylic acid derivative of the formula (I),

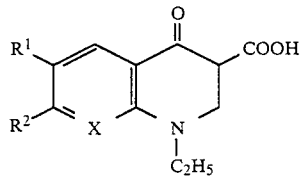

wherein
X is carbon or nitrogen;
$R^1$ is hydrogen or fluorine;
$R^2$ is methyl, piperazino or methylpiperazino group; or $R^1$ and $R^2$ together are a methylenedioxy group; and 0.01 to 95% by weight of a tetracycline derivative of the formula (II),

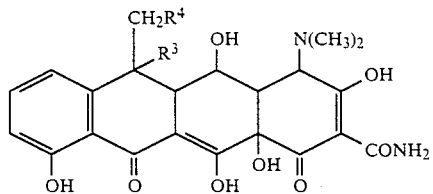

wherein $R^3$ and $R^4$ are hydrogen; or
$R^3$ and $R^4$ together represent an additional chemical bond, in 20:1 to 1:50 ratio of the compound of the formula (I) to the compound of the formula (II), optionally in an admixture with an amount required to 100% by weight of an inert, solid or liquid carrier.

2. A composition as claimed in claim 1 which comprises a quinolinecarboxylic acid derivative or naphthyridinecarboxylic acid derivative of the formula (I), and doxycycline (4-dimethylamino-1,11-dioxo-6-methyl-1,4,4a,5,5a,6,11,12,12a,-octahydro-3,5,10,12,12a-pentahydroxy-2-naphthacenecarboxamide) as active ingredients in a ratio of 5:1 to 1:50.

3. A composition as claimed in claim 2, which comprises norfloxacin (1,4-dihydro-1-ethyl-6-fluoro-4-oxo-7-piperazinoquinoline-3-carboxylic acid) and doxycycline as active ingredients.

4. A composition as claimed in claim 1, which comprises oxolinic acid (1,4-dihydro-1-ethyl-6-7-methylenedioxy-4-oxoquinoline-3-carboxylic acid) and methacycline (4-dimethylamino-1,11-dioxo-6-methylene-1,4,4a,5,5a,6,-11,12,12a-octahydro-3,5,10,12,12a pentahydroxy-2-naphtacenecarboxamide) as active ingredients in a ratio of 5:1 to 1:2.5.

5. A composition as claimed in claim 1, which comprises the active ingredients in 1:1 ratio.

6. An antimicrobial method of treatment which comprises the step of administering to an animal subject in need of said treatment, a therapeutically effective amount of the synergistic, antimicrobial pharmaceutical composition defined in claim 1.

* * * * *